United States Patent [19]

Indrebo

[11] Patent Number: 4,880,102
[45] Date of Patent: Nov. 14, 1989

[54] DEVICE FOR THE TRANSFER OF ARTICLES FROM A FIRST TO A SECOND CONVEYOR

[76] Inventor: Leidulf Indrebø, Simlevn. 28, N-3152 Jersøy, Norway

[21] Appl. No.: 254,480
[22] PCT Filed: Jan. 21, 1988
[86] PCT No.: PCT/SE88/00019
  § 371 Date: Nov. 7, 1988
  § 102(e) Date: Nov. 7, 1988
[87] PCT Pub. No.: WO88/05416
  PCT Pub. Date: Jul. 28, 1988

[30] Foreign Application Priority Data
  Jan. 23, 1987 [SE] Sweden ................ 8700279

[51] Int. Cl.$^4$ ........................... B65G 57/00
[52] U.S. Cl. ................ 198/418.3; 198/470.1; 198/471.1; 198/474.1
[58] Field of Search ............ 198/418.3, 461, 470.1, 198/471.1, 474.1, 476.1, 477.1, 792, 803.5, 408, 472.1, 802

[56] References Cited

U.S. PATENT DOCUMENTS

| | | | |
|---|---|---|---|
| 1,696,360 | 12/1928 | Peyser | 198/474.1 |
| 3,386,558 | 6/1968 | Benatar | 198/408 |
| 3,777,453 | 12/1973 | Zimmermann et al. | 198/471.1 |
| 4,050,574 | 9/1977 | Chenevard et al. | 198/471.1 |
| 4,164,997 | 8/1979 | Mueller | 198/792 |
| 4,394,899 | 7/1983 | Fluck . | |
| 4,469,217 | 9/1984 | Meyer et al. | 198/792 |
| 4,506,779 | 3/1985 | Seragnoli | 198/471.1 |
| 4,558,778 | 12/1985 | Cristiani | 198/471.1 |

FOREIGN PATENT DOCUMENTS

| | | |
|---|---|---|
| 2551538 | 5/1977 | Fed. Rep. of Germany . |
| 2905376 | 8/1980 | Fed. Rep. of Germany ... 198/474.1 |
| 1560748 | 2/1980 | United Kingdom . |
| 2069440 | 8/1981 | United Kingdom . |

*Primary Examiner*—Joseph E. Valenza
*Attorney, Agent, or Firm*—Young & Thompson

[57] ABSTRACT

Device for transferring articles, preferably absorption bodies (A) intended for diapers or corresponding articles, from a first conveyor (1), on which the articles are advanced with first given spacing (a) therebetween, to a second conveyor (2), on which the articles are advanced with a second given spacing (b) therebetween, which device (4) includes a plurality of transporting devices which are rotatable about a rotational axis and which during their rotation are intended to collect articles (A) from a first conveyor (1) at a first location along the rotational path of said transporting devices, and to retain these articles until reaching on the path a second location at which the respective articles (A) are deposited onto the second conveyor (2). According to the invention the speed of each articles transporting device around the aforementioned rotational path is varied during each revolution thereunder by means of a mechanism which superimposes on a primary rotational movement of constant speed of the article (A) at least one secondary movement which is co-directional with the primary rotational movement during a given part of the revolution and counter-directional to the primary rotational movement during a further part of the revolution.

4 Claims, 4 Drawing Sheets

DEVICE FOR THE TRANSFER OF ARTICLES FROM A FIRST TO A SECOND CONVEYOR

The present invention relates to a device which is intended for transferring articles, preferably absorbent bodies intended for diapers or the like, from a first conveyor to a second conveyor, and which comprises a plurality of transporting devices which are capable of rotation about a rotational axis and which during their rotation are intended to collect articles from a first conveyor at a first location on the rotational path and to hold the articles firmly until reaching a second location on said path, at which location the articles are transferred to the second conveyor. More specifically the invention relates to a device, which transfers articles successively to the second conveyor at a mutual spacing between the articles different to the corresponding spacing on the first conveyor.

With known arrangements of similar kinds the transporting devices comprises a plurality of suction openings which are arranged circumferentially around a drum and which are connected with a source of vacuum along part of the curvilinear path rotated by the drum, wherewith absorption bodies or pads are sucked firmly in the openings and accompany the drum in its rotary movement and are subsequently deposited onto a continuous conveyor consisting of liquid-impermeable material. With an arrangement of this kind, the spacing between respective absorption bodies deposited on the moving conveyor can be varied, by changing the rotational speed of the drum and/or by changing the forward speed of the moving conveyor.

However, when the distance between the advanced absorption bodies to be picked up by the drum is short in relation to the interspacing desired between respective bodies when deposited onto the moving conveyor, these variation possibilities are, in many instances, insufficient to fulfill requirements and desiderata related with the technicalities of manufacture. For example, when manufacturing diapers or corresponding products which incorporate absorption bodies, or pads, it is difficult when using machines known hitherto to fulfill technical manufacturing requirements relating to the speed of manufacture.

The object of the present invention is to eliminate these drawbacks and to provide an arrangement for transferring articles from a first conveyor to a second conveyor, with which the articles are deposited at an interspacing which is different to the interspacing of the articles when collected.

This object is achieved in accordance with the invention by means of an arrangement having the characteristic features set forth in claim 1. This arrangement affords a neat and particularly flexible solution to the aforesaid problems. The construction is also relatively simple, robust and reliable and is therewith also favourable from the aspect of manufacture.

The independent claims define an advantageous embodiment of the invention in which the article transporting devices are carried on arms which are pivotally mounted in a rotatable housing and the outer ends of which are movable towards and away from one another during rotary movement of the housing and which will thus be located at varying distances from one another during a full turn of the housing, e.g. will lie very close together when collecting articles and at a maximum distance apart when depositing articles.

So that the invention will be more readily understood, a preferred embodiment of an article transfer device constructed in accordance with the invention will now be described with reference to the accompanying drawings, in which FIG. 1 illustrates a part of a diaper manufacturing plant in which an inventive article transfer device is used;

Figure 1:
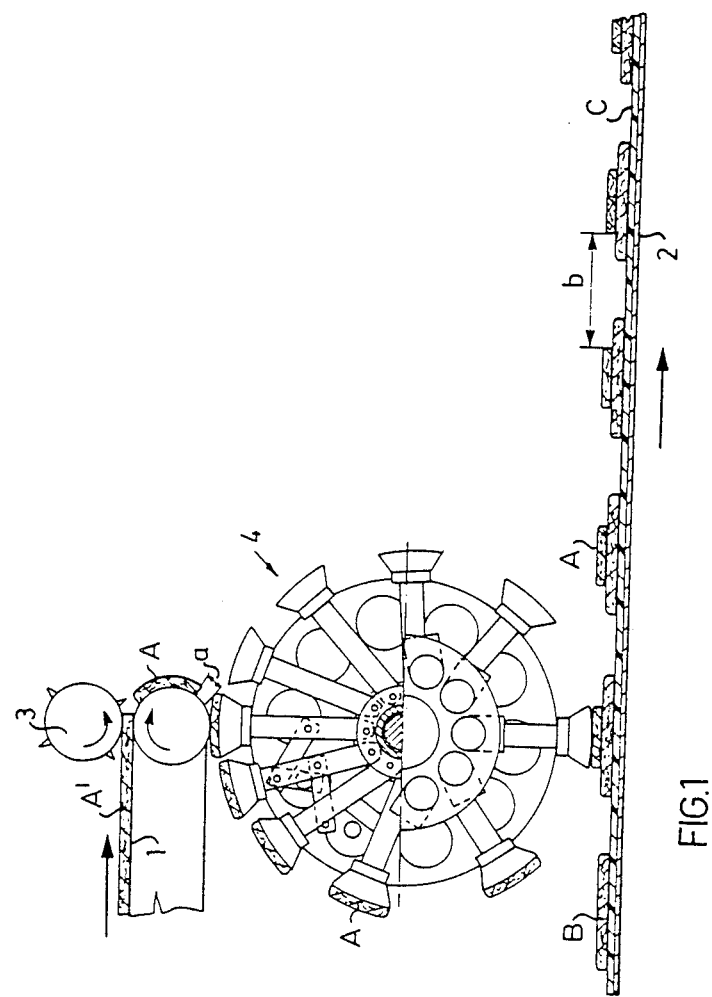

FIG. 1 illustrates an application of the invention in which absorption bodies A are transferred from a first conveyor 1 to a second conveyor 2 which advances absorption bodies B placed on a liquid impermeable material C, the absorption bodies B being less compact than the bodies A. Arranged upstream of that part of the diaper manufacturing plant illustrated in FIG. 1 are compacting rolls between which the continuous web of absorption material A is compacted prior to reaching the cutting roll 3, shown in FIG. 1, which cuts the web A' into absorption bodies A. The absorption material and the bodies A are retained on the conveyor 1, by connecting the conveyor in a known manner to a source of vacuum, so as to hold the bodies firmly by suction. As will be seen from FIG. 1, the spacing a between respective bodies A on the conveyor 1 is very small, and in practice in the order of 10 mm.

The bodies A are transferred from the conveyor 1 to the conveyor 2 by means of an inventive device 4, the distance b between mutually adjacent bodies A on the second conveyor being large and in practice in the order of 300 mm.

Thus, the illustrated device 4 collects the bodies A at a mutual interspacing a at the terminal location of the conveyor 1 adjacent the device and, subsequent to rotating through 180°, deposits the bodies at a mutual interspacing b which is more wider than the interspacing a.

The principle construction of the device 4 will now be described with reference to FIG. 2, which illustrates schematically the main components of the preferred embodiment of the inventive device.

It will be seen from this Figure that the article transfer device includes a plurality of arms 5, the outer ends of which are intended to carry article transporting devices and the inner ends of which are pivotally journalled to a rotatable hub or housing, which also carries the journal shafts for drive gears 6 and intermediate gears 7 which engage a fixed central gear wheel. Each shaft of respective drive gears is firmly connected to a crank web 8, the outer end of which is connected to a toggle lever or link 9. The other end of the toggle link is connected to one of the arms 5 at a distance from the inner end thereof.

The device functions in the following manner: the hub or housing is rotated at a constant speed. Because the drive gears 6, the rotational shafts of which accompany rotation of the housing, are in engagement with the central, fixed gear wheel through the intermediary of respective intermediate gears 7, the fixed gear wheel will also be rotated about its journal shafts in the housing as the housing rotates about the central gear wheel.

Figure 2:
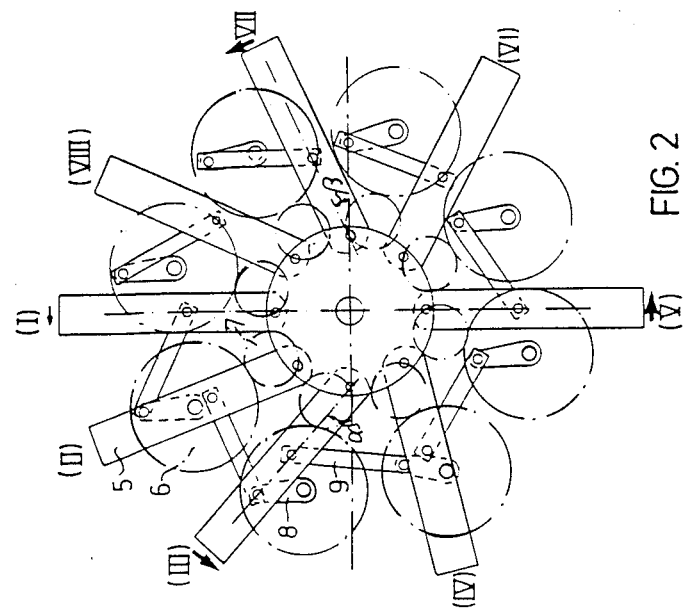
FIG. 2 illustrates the principle construction of one embodiment of an inventive transfer device.

Thus, if the housing is rotated anticlockwise, as indicated by arrows in FIG. 2, the drive gears 6 will rotate in a clockwise direction. The crank webs 8 will therewith also rotate in a clockwise direction, wherewith the toggle links 9 are displaced and therewith alter the distance between drive-gear shaft and arm during rotation of the housing.

In the case of the FIG. 2 embodiment, the drive gear 6 has the same pitch as the central gear wheel, and hence the drive gear will turn through one complete revolution as it travels around the central gear wheel. It will be seen from this Figure that the arm 5 has two diametrically opposed positions in which it extends parallel with the crank web 8, these positions corresponding to those locations at which the articles are collected and deposited respectively in FIG. 1. A line which is drawn through the rotational shaft of the drive gear 6 and the pivot point of the link 9 on the arm 5 when the arm 5 occupies either of the aforesaid positions will extend perpendicularly to the longitudinal axis of the crank web.

All eight arms 5 and mechanisms 6-9 are mutually identical, and hence the eight different arm positions illustrated in FIG. 2 correspond to eight successive positions of each arm 5. Consequently, the movement performed by a single arm 5 during one revolution of the housing will be described hereinafter with reference to these eight positions I-VIII of the arms 5.

Between positions I and II the housing, and therewith the journalled inner ends of respective arms 5, has turned through one quarter of a revolution. The crank web 8 has, at the same time, rotated one quarter of a revolution around the shaft of the drive gear 6, so that the crank web 8 and the toggle link 9 are essentially in line with one another, which means that in this position the pivot point of the link 9 in the arm 5 is displaced essentially to a maximum from the shaft of the drive gear.

Between the positions III-V, in which latter position the housing has rotated one half of a revolution, the distance between drive-gear shaft and the pivot point of the toggle link on the arm decreases and in position V will have the same value as in position I, which means that the arm again extends radially. Between the positions V-VII, which correspond to further rotation of the housing through one quarter of a revolution, the distance between the drive-gear shaft and the pivot point of the link 9 on the arm decreases still further, such that in position VII the crank web is again in line with the toggle link and also overlaps the same, thereby achieving in this position the smallest possible distance between drive-gear shaft and the pivot point of the toggle link on the arm.

The distance between drive-gear shaft and the link pivot-point on the arm again increases during rotation of the housing through the last quarter revolution.

Thus, as the housing or hub rotates, the arms 5 will swing about their journals on both sides of an intermediate position in which the arms extend radially. The terminal positions of this pivotal movement are reached at the two positions in which the crank web and the toggle link are in line with one another, i.e. at positions III and VII. The intermediate position is attained in positions I and V, which therefore means that the inwardly located ends of the arms will precede the outer ends of said arms during the first half of a revolution, and that the outer ends will precede the inner ends during the second half of a revolution.

Simple consideration of the FIG. 2 illustration will show in this regard that the outer ends of the arms must move faster than the inner ends thereof at least between positions IV and V, while the reverse is the case with regard to movement between positions VIII and I. In actual fact, as a result of this swinging or pivotal movement, the peripheral speed of the outer ends of respective arms decreases in relation to the peripheral speed of the outer end of an arm rigidly fixed to the housing during corresponding rotation between positions I-III, whereafter the speed increases during rotation between positions III-VII and again decreases between positions VII-I, as indicated in FIG. 2 with arrows of varying sizes. The relative changes in the peripheral speed of the outer ends of respective arms is zero at positions III and VII, the arms moving at a peripheral speed which corresponds to the rotational speed of the housing in these positions, whereas the change in speed is at maximum at positions I and V.

It will be understood that if the outer end of the toggle link 9 had been guided to execute a linear reciprocating movement instead of an oscillatory pivotal movement, a curve drawn to represent the changes in speed would have been a fully sinusoidal curve and the terminal positions would have been reached after rotation of the crank web through precisely 90° and 270° respectively. However, since the oscillatory pivotal movement of the arms 5 follows a circular arcuate path, the position III will be reached in reality when the housing, and therewith the drive-gear shaft, has rotated through more than 90° and the position VII will be reached when the drive-gear shaft has rotated through more than 270° to the same extent as that rotated by the drive-gear shaft in excess of 90° in order to reach the position III. The positions I and V, however, will still be reached subsequent to rotation of the drive-gear shaft through 360° and 180° respectively, and hence the oscillatory movements executed by the arms 5 will have different amplitudes and speeds on either side of the intermediate position defined by the positions I and V. Thus, the oscillation amplitudes, and therewith the changes in speed are greatest during the first half of a revolution executed by the drive gear. This is best seen by comparing the swinging angles and in positions III and VII respectively, which constitute the turning points of the oscillatory movement of the arms.

Movement of the arms is thus a composite movement which consists of a rotary movement at constant speed around the rotational axis of the housing and the aforesaid oscillatory movement, which is superimposed on the constant-speed rotary movement. Thus, during one revolution around the rotational axis of the housing, the outer ends of arms 5 will move at different peripheral speeds relative to one another, except in the positions III and VII. The outer ends of respective arms will therefore be accelerated during the first half of a revolution and decelerated during the second half thereof, thereby causing the distance between respective arms to increase during the first half of a revolution and to decrease during the second half. The peripheral speed of the arms 5 is at a maximum at positions V and at a minimum at position I.

In the case of the illustrated exemplifying embodiment, the drive gear has the same pitch as the fixed central gear wheel. If the pitch is changed the speed at which the drive-gear shaft rotates will change to a corresponding extent, and therewith also the superimposed oscillatory movement. For example, if the drive-gear shaft is rotated at twice the speed of the housing, the position V will be reached after only one quarter of a revolution, as will readily be seen.

These variations can also be achieved, by rotating the central gear wheel instead of changing the pitch of the drive gear.

Figure 3:
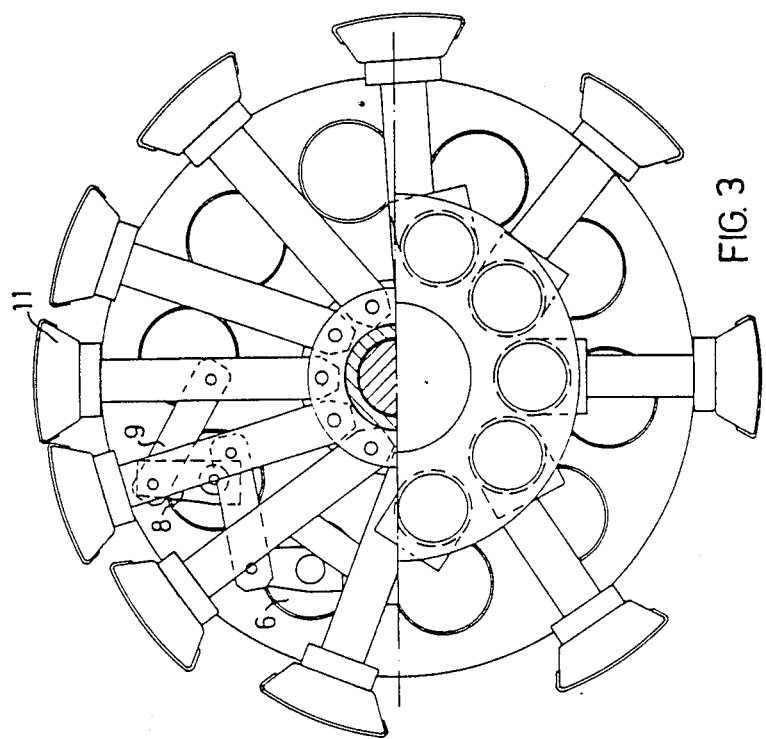
FIG. 3 is a front view, partly in section, of one embodiment of an inventive transfer device.

Two variants of an embodiment of an inventive article transfer device will now be described with reference to FIGS. 3–5, in which the same reference signs as those used in FIGS. 1 and 2 have been used to identify equivalent elements.

The variant illustrated in FIGS. 3 and 4 fully coincides in principle with the embodiment described with reference to FIG. 2, but differs constructionally insomuch as the article transfer device has ten arms 5 instead of eight. Each of these arms carries a respective transporting device in the form of a suction box 11 which, via flexible pipes shown in broken lines in FIG. 4, is connected to pipes located in a housing 12 and communicating with a vacuum chamber or sub-pressure chamber 13.

Figure 4:
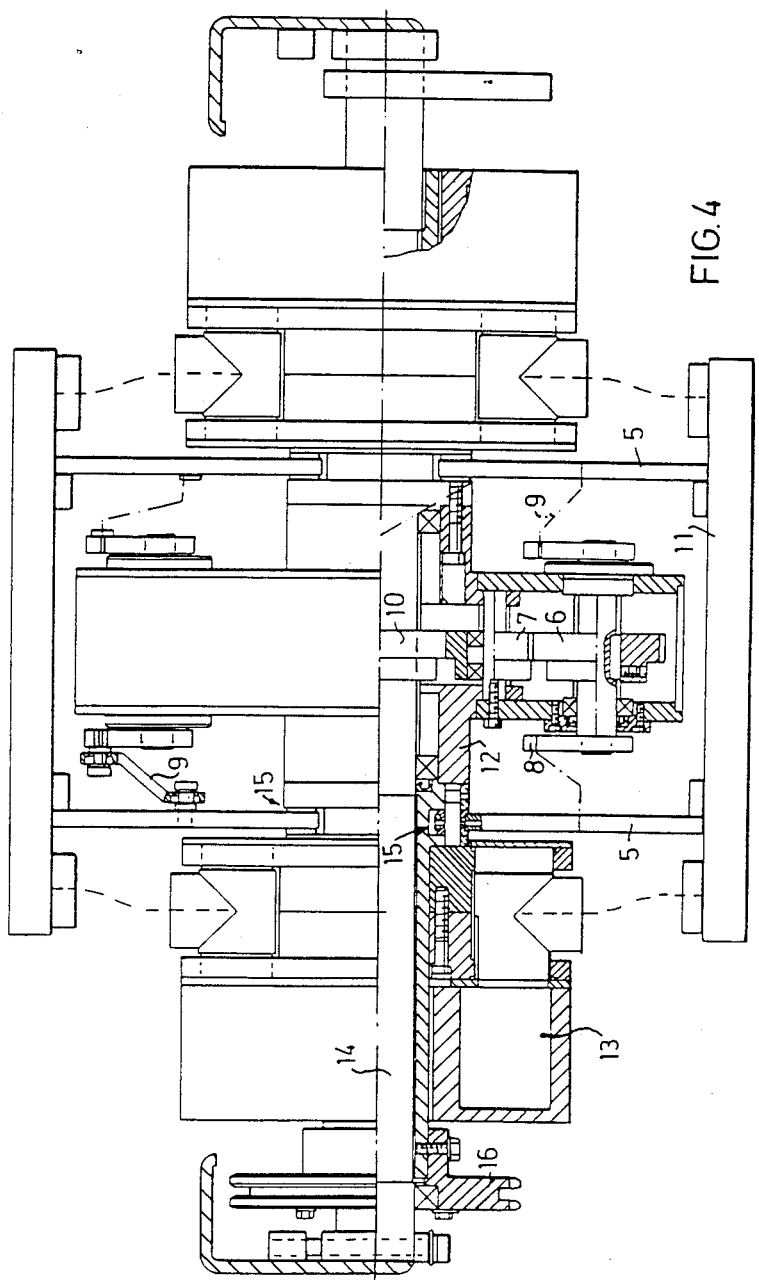
FIG. 4 is a side view, partly in section, of the device illustrated in FIG. 3.
Figure 5:
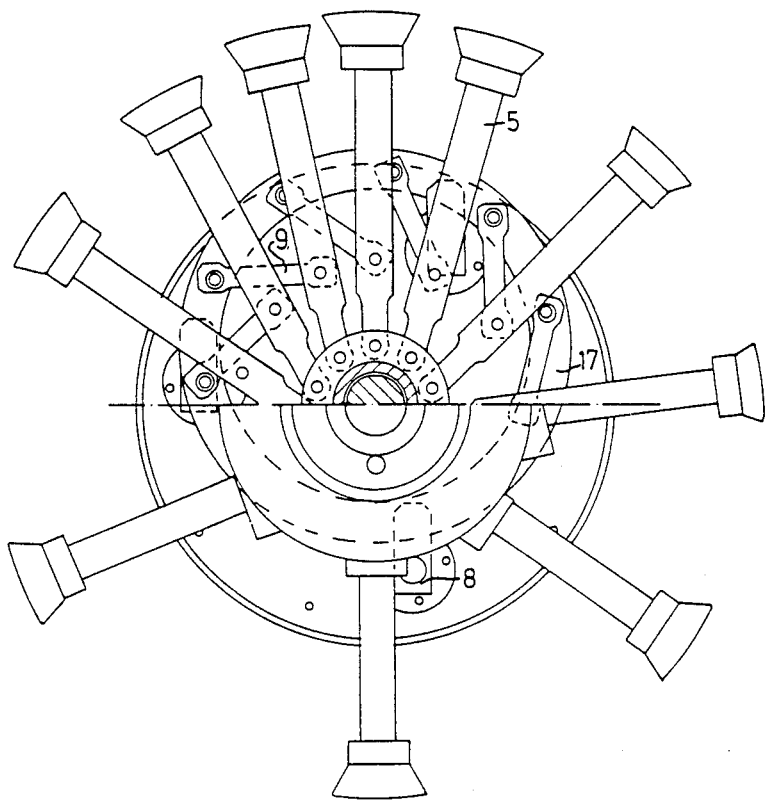
FIG. 5 illustrates an inventive variant of the embodiment illustrated in FIG. 3.

As shown in FIG. 4, each suction box 11 is carried by a pair of arms 5 provided with associated crank webs, which are mounted on respective ends of the shaft carrying the drive gear 6, and toggle links or levers 9 which are inclined to the vertical plane, so as to ensure that successive link mechanisms 8, 9 will no catch in one another or strike against each other as the arms rotate. The drive gear 6 engages a central gear wheel 10 through the intermediary of an intermediate gear 7, said gear wheel 10 being fixedly connected to a fixedly journalled shaft 14.

The inner ends of the arms 5 are pivotally journalled at 15 to a hub which is journalled for rotation about the shaft 14 and which forms the housing 12 together with ring-shaped walls, which support the intermediate gears 7 and the drive gears 6, and ring-shaped elements which incorporate the aforesaid vacuum pipes. The hub is closed at one end thereof by a drive wheel 16 by means of which the hub, and therewith the whole of the housing 12, can be rotated.

The vacuum chamber 13 of the illustrated embodiment is rotatably journalled relative to the hub, so as not to rotate together therewith. When the chamber is given a semi-circular arcuate configuration, the suction boxes will only hold the articles during trhe desired one half of a revolution.

As will best be seen from FIG. 2, when the drive gear has the same rotational speed as the housing, the ends of respective crank webs will move in a circle around the rotational axis of the housing. This fact has been utilized in the FIG. 5 variant, by replacing some of the crank webs and the drive gears with a ring 17 which is carried by three crank webs 8 and three drive gears 6.

In the case of the illustrated variants, the transporting devices will also be displaced slightly in a radial direction, as a result of the oscillation of the arms. Consequently, the radially outermost positions of the transporting devices are located in the positions I and V, i.e. respectively in the article collecting position and the article depositing position shown in FIG. 1 in respect of articles A, which reduces the risk of the arms unintentionally striking the articles carried by the conveyors 1 and 2. It is, of course, possible to arrage the arms 5 for rotation about the rotational axis of the housing, but this solution is less practicable due to the space that would be required.

In the case of another variant (not shown) the transporting devices may be carried on carriages which run on tracks around the periphery of a circular housing and which are connected to toggle links and crank webs through the intermediary of radially and downwardly extending arms. In this case, the connection between arms and toggle links in the radial direction shall permit relative displacement between these elements.

In the case of still another variant (not shown) the toggle links are replaced with grooves or slots located in respective arms and pins which are pivotally mounted on the ends of respective crank webs and which move in the grooves or slots. In this case the changes in speed during a revolution can be selected with far greater variation than with the previously described constructions, by compensurate configuration of the grooves. For example, a groove which extends radially in the intermediate position will result in a fully sinusoidal speed curve, whereas a circular groove will prevent the arm from oscillating at all.

It will be understood that the described preferred embodiment can be modified within the scope of the invention. For example, the drive gears may be in direct meshing engagement with the central gear wheel or may be driven by some external power source. Furthermore, the arms may comprise telescopically displaceable components such as to enable the device to be adapted to differing distances between the first and second conveyors. In the case of large dimensions, the gear drive may be replaced with a chain drive, so as to enable drive wheels of smaller dimensions to be used.

The inventive device can be easily adpated for usages other than with diaper manufacturing machines, for example by providing the arms or the elements which carry the article transporting devices with gripping and holding devices of a kind appropriate for the use intended. For instance, the present inventive device can be used to transfer onto envelopes printed labels which are advanced sequentially in mutual close relationship. The inventive device may, of course, also be used to pick-up articles which are advanced with a wide spacing therebetween and to deposit those articles with a small spacing therebetween.

The scope of the invention is therefore limited solely by the disclosures made in the following claims.

I claim:

1. A device for transferring articles, preferably absorption bodies (A) intended for diapers or corresponding articles, from a first conveyor (1), on which the articles are advanced with a first given spacing (a) therebetween, to a second conveyor (2), on which the articles are advanced with a second given spacing (b) therebetween, which device (4) includes a plurality of transporting devices (11) which are rotatable about a rotational axis and which during their rotation are intended to collect articles (A) from the first conveyor (1) at a first location (I) along the rotational path of said transporting devices, and to retain said articles until reaching on said path a second location (V) at which the respective articles (A) are deposited onto the second conveyor (2), and which device (4) further includes a mechanism (5–10) by means of which the speed of each article transporting device (11) around said rotational path is varied during each revolution therearound and by means of which there is superimposed on a primary rotational movement of constant speed of the article (A) at least one secondary movement which is co-directional with the primary rotational movement during a given part of said revolution and counter-directional to said primary rotational movement during a further part of said revolution, and in which device (4) each article transporting device (11) is carried by a respective arm (5) whose radially inner end is pivotally mounted to a housing (12) which can be rotated around said rotational axis, and whose radially outer end carries said transporting device (11), characterized in that each of the arms (5) is pivotally journalled between its ends to one end of a respective link (9), and in that the device (4) further includes crank webs (8) each of which is rotationally driven by a respective rotatably journalled drive gear (6) which is in engagement, either directly or indirectly, with a centrally located gear wheel (10) which is journalled for free rotation relative to the housing (12), and each of which crank webs (8) co-acts with a respective link (9) in a manner to move, during rotation of the housing (12), the other end of respective links in a circular path relative to the rotational axis of the drive gear, so as to cause the arm (5) to oscillate about its pivot point.

2. A device according to claim 1, characterized in that each arm is connected to an individual drive gear (6) via a link (9) and a crank web (8).

3. A device according to claim 1, characterized in that three drive gears (6) rotationally drive three crank webs (8), the other ends of which are pivotally connected to a ring (17), and in that links (9) connected to respective arms are pivotally connected to the periphery of the ring (17).

4. A device according to claim 1, characterized in that each arm (5) is pivotally journalled to the housing (12) at a location readially outwards of the rotational axis of said housing.

* * * * *